United States Patent [19]

Mosbach et al.

[11] Patent Number: 5,208,155
[45] Date of Patent: May 4, 1993

[54] D-AMINO ACID OXIDASE AND METHOD FOR ISOLATION THEREOF

[76] Inventors: Klaus Mosbach, Rebbergstrasse 83, CH-8102 Oberengstringen, Switzerland; Estera Szwajcer, Tillämpad Biokemi, Kemicentrum, Lunds Universitet, Box 124, S-221 00 Lund, Sweden

[21] Appl. No.: 900,758
[22] PCT Filed: Jan. 10, 1986
[86] PCT No.: PCT/SE86/00006
 § 371 Date: Nov. 5, 1986
 § 102(e) Date: Nov. 5, 1986
[87] PCT Pub. No.: WO86/04087
 PCT Pub. Date: Jul. 17, 1986

Related U.S. Application Data

[63] Continuation of Ser. No. 773,763, Oct. 10, 1991, abandoned, which is a continuation of Ser. No. 373,607, Jun. 30, 1989, abandoned, which is a continuation of Ser. No. 918,251, Nov. 5, 1986, abandoned.

[30] Foreign Application Priority Data

Jan. 11, 1985 [SE] Sweden .................... 8500157

[51] Int. Cl.⁵ .................... C12N 9/06; C12N 11/12
[52] U.S. Cl. .................... 435/191; 435/814; 435/816; 435/179
[58] Field of Search ........... 435/191, 814, 816, 179, 435/174, 189

[56] References Cited

U.S. PATENT DOCUMENTS 3,658,649  4/1972  Arnold et al. ............... 195/29
3,801,458  4/1974  Fildes et al. ............... 195/29
4,486,549  12/1984  Matsumoto et al. .......... 521/53

OTHER PUBLICATIONS

Berg, C. P., et al. (1976) Anal. Biochem, 71, 214-222.
Biotechnology Applications and Research (eds. Cheremisino P. N., et al., Technomil Pub. Co., Inc., 1985, pp. 21, 541-557 Szwajcer F., et al. (1985) Biotechnol. Lett. 7(1), 1-7.

Primary Examiner—Robert A. Wax
Assistant Examiner—Keith D. Hendricks
Attorney, Agent, or Firm—Birch, Stewart, Kolasch & Birch

[57] ABSTRACT

A *Trigonopsis variabilis* D-amino acid oxidase in substantially pure form and active against cephalosporin C is disclosed. This D-amino acid oxidase is isolated from *Trigonopsis variabilis* by a method which is performed in three steps, namely:
(a) acidifying and heating a crude cell extract of *Trigonopsis variabilis* to obtain a precipitate and supernatant fraction;
(b) treating said supernatant fraction obtained in step (a) with sufficient ammonium sulfate to obtain a second precipitate, said second precipitate containing the D-amino acid oxidase of claim 1; and
(c) resuspending the precipitate obtained in step (b) and collecting the D-amino acid oxidase by isoelectric precipitation.

5 Claims, 1 Drawing Sheet

D-AMINO ACID OXIDASE AND METHOD FOR ISOLATION THEREOF

This application is a continuation of application Ser. No. 07/773,763 filed on Oct. 10, 1991, which is a continuation of application Ser. No. 07/373,607 filed on Jun. 30, 1989, which is a continuation of Ser. No. 06/918,251 filed on Nov. 5, 1986, all now abandoned.

The present invention relates to a D-amino acid oxidase which is active against cephalosporin C, and a method for isolating it from *Trigonopsis variabilis*.

There is a long-standing considerable interest in using amino acid oxidase activity for forming o-keto acids from their corresponding amino acids since these are of interest as a nutritional supplement for patients suffering from kidney insufficiency. Both D-amino acid oxidase activity found in the yeast *Trigonopsis variabilis* (Brodelius, P., Nilsson, K., and Mosbach, K., 1981, Appl. Biochem, Biotechnol. 6, 293-308) and L-amino acid oxidase activity found in the bacterium *Providencia* (Szwajcer, E., Brodelius, P., and Mosbach, K. (1982). Enzyme Microb. Technol. 4, 409-413) have been used. D-amino acid oxidase also exhibited activity against cephalosporin C, by oxidatively deaminating the latter to keto adipic 7-aminocephalosporanic acid. The same activity was also reported in U.S. Pat. No. 3,658,649. However, the extract used was obtained only by ammonium sulfate precipitation and thus represents crude preparation comprising several amino acid oxidases A number of different organisms have been examined in respect of the latter activity, including *E. coli, Pseudomonas* species, *Aerobacter* species, *Candida tropicalis, Penicillium rocforti, Aspergillus flavus* and *A. niger, Neurospora crassa, Nocardia, Citrobacter* and *Trigonopsis variabilis*. Only *Trigonopsis variabilis* and *Citrobacter* could deaminate cephalosporin C to keto adipic 7-aminocephalosporanic acid. The activity found in *Citrobacter* was very low and appeared to be membrane-bound, while the enzyme from *Trigonopsis* was present in the cytoplasm and at a much higher level. It should be mentioned in this context that the activity against cephalosporin C was also found with the enzyme obtained from hog kidney (Mazzeo, P., and Romeo, A. (1972). J. C. S. Perkin I(P3), 2532). 7-Aminocephalosporanic acid has great industrial interest as basic moiety for the preparation of semisynthetic cephalosporins by analogy with 6-aminopenicillanoic acid for the preparation of semisynthetic penicillins. An acylase has been reported in the literature (Shibyva, Y., Matsumoto, K., and Fuji, T. (1981). Agr. Biol. Chem. 45, (1561-1567) which hydrolyzes the side-chain of glutaryl-7-aminocephalosporanic acid. The latter compound is spontaneously formed from keto adipic-7-aminocephalosporanic acid by the hydrogen peroxide simultaneously formed. The following diagram illustrates the formation of 7-aminocephalosporanic acid, under the influence of two enzymes:

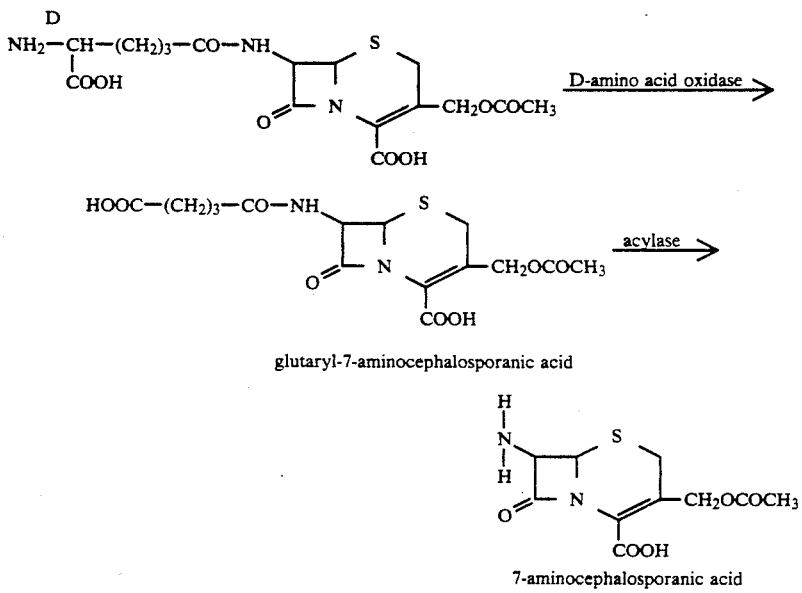

glutaryl-7-aminocephalosporanic acid 7-aminocephalosporanic acid

The present invention has for its object to produce a *Trigonopsis variabilis* D-amino acid oxidase in substantially pure form and active against cephalosporin C.

Another object of the invention is to provide a method for isolating a D-amino acid oxidase from *Trigonopsis variabilis*.

The simple method for purifying D-amino acid oxidase to homogeneity according to the invention is carried out in three steps. Thus, the method is characterized in that it comprises (a) acidifying and heating a crude cell extract of *Trigonopsis variabilis* to obtain a precipitate and supernatant fraction;

(b) treating said supernatant fraction obtained in step (a) with sufficient ammonium sulfate to obtain a second precipitate, said second precipitate containing the D-amino acid oxidase of claim 1; and (c) resuspending the precipitate obtained in step (b) and collecting the D-amino acid oxidase by isoelectric precipitation.

The acidification according to step (a) above can be performed by adding acetic acid to the crude cell extract. The cell extract is acidified to a pH of about 4 to 6, preferably about 5.1 to 5.3 and most preferably about 5.3.

In a further embodiment, any precipitate formed after acidification is removed prior to heating. Further, D,L-methionine can be added prior to heating, preferably in an amount to obtain a final concentration of about 25 mM.

The crude extract is heated in step (a) above to a temperature of about 40° to about 60° C., preferably about 40° to about 50° C. and most preferably to about 50° C.

In another preferred embodiment, the supernatant fraction of step (a) is dialyzed prior to the treatment with ammonium sulfate, preferably against a buffer comprising 20 mM sodium pyrophosphate, pH 8.3.

In still another preferred embodiment, the supernatant fraction of step (a) is concentrated after dialysis prior to the treatment with ammonium sulfate. This concentration is preferably accomplished by evaporation.

The treatment with ammonium sulfate may in a preferred embodiment comprise (i) adding ammonium sulfate to said supernatant fraction to obtain an ammonium sulfate concentration of about 30% by weight and removing the resulting precipitate; and (ii) adding additional ammonium sulfate to the supernatant of (a) to obtain an ammonium sulfate concentration of about 55% and collecting the resulting precipitate.

The second D-amino acid oxidase-containing precipitate in step (c) above can be dialyzed prior to collecting by isoelectric precipitation, preferably against a buffer comprising 20 mM sodium pyrophosphate, pH 8.3.

The isoelectric precipitation comprises:

(a) dialyzing said second precipitate against a buffer that comprises 25 mM sodium acetate, pH 5.1, and removing any precipitate that remains after said dialyzing step; and (b) dialyzing the solution obtained from said dialyzing step against a buffer that comprises 100 mM sodium acetate, pH 4.6, and collecting the purified D-amino acid oxidase precipitate.

The D-amino acid oxidase obtained by the isoelectric precipitation may be further purified by gel electrophoresis.

The invention also comprises an immobilized form of the D-amino acid oxidase, preferably conjugated with cyanogen-bromide-activated Sepharose.

In a further embodiment, the method of the invention is characterized in that (a) cells of *Trigonopsis variabilis* are disintegrated for forming a crude extract which is acidified;

(b) the acidified crude extract is heated to 50° C., and the precipitate formed is removed and the supernatant dialyzed;

(c) the product from (b) is precipitated with ammonium sulfate and dialyzed; and (d) D-amino acid oxidase is isolated by isoelectric precipitation.

In a still further embodiment, the method of the invention comprises:

(a) acidifying a crude cell extract of *Trigonopsis variabilis* by adding acetic acid until the pH of the extract is about 5.3 to form a precipitate and supernatant fraction;

(b) adding D,L-methionine to said supernatant to a final concentration of 25 mM;

(c) heating said supernatant to 50° C. and maintaining it at 50° C. for ten minutes to form a second precipitate and supernatant fraction;

(d) dialyzing said supernatant obtained in step (c) against 20 mM sodium pyrophosphate buffer, pH 8.3;

(e) adding solid ammonium sulfate to the solution prepared in step (d) to a final concentration of 30% and removing the resulting precipitate;

(f) adding solid ammonium sulfate to the solution prepared in step (e) to a final concentration of 55% and collecting the resulting precipitate;

(g) dialyzing said precipitate prepared in step (f) first against 20 mM sodium pyrophosphate buffer, pH 8.3, then against 25 mM sodium acetate buffer, pH 5.1, and removing any undissolved precipitate that remains after dialysis; and (h) dialyzing the solution obtained in step (g) against 100 mM sodium acetate buffer, pH 4.6, and collecting the D-amino acid oxidase-containing precipitate.

The invention will now be described in greater detail in an Example, with reference to the accompanying drawings.

Materials and Methods

Materials

Figure 1:
FIG. 1 shows polyacrylamide gel electrophoresis of purified D-amino acid oxidase Gel electrophoresis of 25 μg of pure protein in sodium dodecyl sulphate shows only one protein band (the dark minor band seen to the left indicates the borderline of the two "fused" gels). The marker added to the gels was cut out prior to protein staining.

Peroxidase (Type II, from horse-radish), all amino acids, cephalosporin C, dinitrophenyl hydrazine and o-dianisidine were obtained from Sigma (St. Louis, Mo, USA). Acrylamide and N,N'-methylene-bis-acrylamide were obtained from Merck-Schuchardt (Munich, Germany). N,N,N',N'-tetramethylethylenediamine, ammonium persulphate and sheets precoated with 0.25 mm of silica gel $F_{254}$ were obtained from Merck (Darmstadt, Germany). Growth media were products from Difco (Detroit, USA). The oxygen electrode was obtained from Rank Brothers Bottisham (Cambridge, Great Britain).

Methods

Analytical isoelectric focusing in polyacrylamide gel was carried out, using the LKB 1804-101 system. The carrier ampholytes used had a pH range of 3.5-9.5. Isoelectric focusing was performed in accordance with a leaflet from LKB regarding ampholine PAG plates for analytical electrofocusing on polyacrylamide gels (LKB-Produkter AB, Bromma, Sweden, 1979).

Iron was determined at the Department of Analytical Chemistry, University of Lund, by atomic absorption spectrophotometry.

Culture Conditions

The microorganism used in the studies was the yeast *Trigonopsis variabilis*, the same as used by Brodelius et al. (Brodelius, P., Nilsson, K., and Mosbach, K. (1981). Appl. Biochem. Biotechnol. 6, 293-308). Larger batches of cells were obtained from 8-liter cultures in a fermentor. The growth medium was composed of yeast extract (1%), malt extract (1.5%) supplemented with 0.2% DL-methionine, pH 6.0, and incubated for 44 hours at 28° C. The stock culture was maintained on slants made up of the same medium containing 2% agar. The cells were collected by centrifugation at 4000 g for 30 min., washed and stored in the frozen state until used. The average yield of the cells from different fermentations was in the range of 45-50 g cell paste.

Streptomyces and Nocardia strains were obtained from the Department of Microbiology, Institute of Immunology, Wroclaw, Poland. Bacteria and fungi were obtained from ATCC.

Electrophoresis

For analytical purposes, disc polyacrylamide gel electrophoresis was carried out according to Hedrick and Smith (Hedrick, J. L., and Smith, A. J. (1968). Arch. Biochem. Biophys. 126, 155-164) and according to Laemmli (Laemmli, U. K. (1970). Nature 227, 680-685) for SDS-containing gels. Electrophoresis was performed at 8°-10° C. Initially, a low current of 2 mA per tube was supplied until the dye had migrated into the separation gel, whereupon the current was increased to a constant value of 4 mA per tube. The diameter and length of the tube was 0.8 cm and 9.5 cm, respectively. For locating the protein, the gels were stained with Coomassie Brilliant Blue R.

Enzymatic activity on the gels was located according to Hedrick and Smith (see above), the gels being stained by detection of the formed hydrogen peroxide, using o-dianisidine. The gels were incubated in 0.1 M sodium phosphate buffer, pH 7.2, containing 5 mM cephalosporin C (or other amino acids), peroxidase (0.025%), and o-dianisidine (0.025%). Incubation was carried out for 30-60 min. until the reddish brown dye had been formed.

For preparative enzyme isolation, a special equipment has been designed by the inventors. The diameter of the glass tube was 2 cm and the length of the tube was 14 cm. The gel (8% polyacrylamide) was prepared according to Hedrick and Smith (see above), using 0.19 M Tris-glycine buffer, pH 8.3. The upper gel was polymerized in the presence of ammonium persulphate and TEMED instead of riboflavin (the amount of catalysts was taken according to Laemmli (see above)). Electrophoresis was carried out for 3-4 hours at 10° C., using 20 mA during the first 30 min., followed by 40 mA.

Molecular Weight Determination

The molecular weight of the protein was determined as described by Hedrick and Smith (see above) and SDS gel electrophoresis was performed according to Laemmli (see above). For the first method, use was made of molecular weight markers for non-denaturated polyacrylamide gel electrophoresis (SIGMA) and, for the latter, use was made of SDS molecular weight markers. Protein determination was made according to Lowry et al. (Lowry, O. H., Rosebrough, N. J., Ferr, A. L., and Randall, R. J. (1951). Biol. Chem. 193, 265-275).

Analysis in Respect of D-Amino Acid Oxidase Activity

By determining the rate of oxygen consumption with a Rank oxygen electrode, D-amino acid oxidase was assayed at 50° C. for 5-10 min., during which time no enzyme denaturation took place. The assay mixture contained in a final volume of 2 ml, 1.8 ml (20 mM) sodium pyrophosphate, pH 8.0, 0.1 ml (100 mM) cephalosporin C and the appropriate amount of enzyme to provide the correct initial rate of oxygen consumption. 1 unit (U) corresponds to the uptake of 1 μmole of oxygen/min. under the conditions used. From time to time, the activity was also checked by measuring the amount of formed keto acid with a colorimetrical method, at 30° C., using 2,4-dinitrophenyl hydrazine as well as with o-dianisidine-peroxidase (see above).

EXAMPLE

Purification of D-Amino Acid Oxidase From *Trigonopsis Variabilis*

All operations were performed at 5° C.

Step 1

Preparation of Crude Extract 32 g of frozen cell paste (−20° C.) was thawed and suspended in 1.5 volumes of 20 mM sodium pyrophosphate buffer, pH 8.3. The cell suspension was mixed with an equal volume of powdered dry ice and disintegrated in a mixer. D-amino acid oxidase was released together with other soluble proteins. The disrupted cells were centrifuged for 30 min. at 12,000 g. The disrupted cells were washed several times with a new aliquot of buffer and centrifuged. The collected supernatants were acidified to pH 5.3 with 2 m acetic acid, and the resulting precipitate was removed by centrifugation for 30 min. at 12,000 g.

Step 2

Heat Precipitation

To the acidic supernatant (730 ml) from Step 1 was added 25 mM of DL-methionine to protect the enzyme. The supernatant was heated to 50° C. and maintained at this temperature for 10 min. in a water bath. The resulting precipitate was spun down for 30 min. at 12,000 g and the precipitate was discarded. The supernatant was dialyzed against 20 mM sodium pyrophosphate buffer, pH 8.3, overnight.

Step 3

Ammonium Sulphate Precipitation

The sample from Step 2 was concentrated by blowing warm air over a dialysis bag (containing the sample) to increase the amount of protein per ml (1%). The pH of the sample was lowered with 2 M acetic acid to pH 6.3 and thereafter mixed for 1-2 hours with solid ammonium sulphate. The fraction salted out with 30% ammonium sulphate was left to form a precipitate and thereafter centrifuged for 30 min. at 12,000 g. The precipitate was discarded and the supernatant (after adjusting to pH 6.0) was mixed with solid ammonium sulphate (55%). The precipitate formed after 2 hours was centrifuged for 30 min. at 12,000 g and dialyzed against 20 mM sodium pyrophosphate, pH 8.3.

Step 4

Isoelectric Precipitation

The sample from Step 3 (10.3 ml) was dialyzed against 25 mM sodium acetate buffer, pH 5.1, for 12 hours. The resulting precipitate was removed by centrifugation for 30 min. at 12,000 g. The precipitate contained traces of enzymatic activity. The supernatant was precipitated once more by dialysis against 0.1 M sodium acetate buffer, pH 4.6, for 12 hours. The precipitate formed contained most of the D-amino acid oxidase activity. The precipitate was dissolved in 20 mM pyrophosphate buffer, pH 8.3, and dialyzed against the same buffer overnight.

Preparative Disc Gel Electrophoresis

The sample from Step 4 was used for the preparative gel electrophoresis. 5 mg of the protein from Step 4 was used for the electrophoretic test. The band showing amino acid oxidase activity against cephalosporin C was cut out and homogenized for 5 min. with a Potter homogenizer (1000 rev./min.) in 20 mM pyrophosphate buffer, pH 8.3, whereupon the suspension obtained was centrifuged at 10000 g for 20 min. The gel was washed 3 times with an equal amount of buffer and the collected supernatants were concentrated by means of warm air, as above, to a final volume of 3 ml and used for further studies.

RESULTS AND DISCUSSION

TABLE 1

Purification of D-amino acid oxidase from Trigonopsis variabilis. The activity was measured against cephalosporin C. The protein content was determined as described by Lowry et al. (see above).

| | Treatment steps | Total activity Units | Protein mg/ml | Specific activity U/mg | Purification Fold | Yield % |
|---|---|---|---|---|---|---|
| 1. | Crude extract | 384 | 3.5 | 0.15 | 1 | 100 |
| 2. | Heat precipitation | 308 | 5.6 | 1.0 | 6.5 | 80 |
| 3. | (NH4)2SO4 precipitation (30–55%) | 300 | 6.0 | 4.9 | 33.0 | 78 |
| 4. | Isoelectric precipitation, pH 4.6 | 154 | 2.8 | 5.8 | 39 | 40 |

The present invention provides a simple method for purifying D-amino acid oxidase to homogeneity. Preparative gel electrophoresis after the isoelectric precipitation step removed two additional weak bands observed on gel electrophoresis. The specific activity decreased from 5.8 U/mg (Table 1) to 3.8 U/mg. It can be assumed that this is due to partial denaturation occurring during extraction or to loss of cofactors not yet identified.

Figure 2:
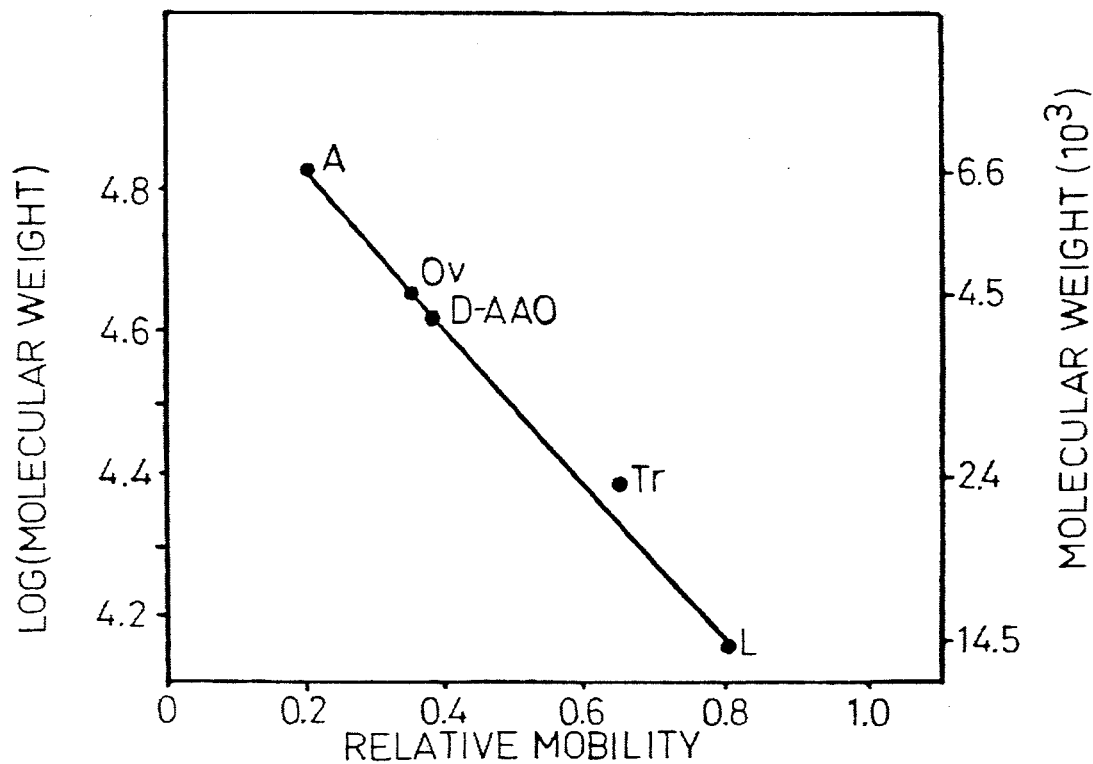
FIG. 2 shows the result of the determination of the molecular weight of D-amino acid oxidase from *Trigonopsis variabilis*. SDS gel electrophoresis was carried out in 12% polyacrylamide according to Laemmli, (Laemmli, U. K. (1970). Nature 227, 680–685). The following protein markers were used: A=albumin (66,000) OV=ovalalbumin (45,000), Tr=trypsinogen (24,000), and L=lysozyme (14,500).

Polyacrylamide gel electrophoresis in sodium dodecyl sulphate yielded a single band (FIG. 1) of a molecular weight of about 43,000 (FIG. 2). The molecular weight of the native protein, determined according to Hedrick and Smith (Hedrick, J. L., and Smith, A. J, (1968). Arch. Biochem. Biophys. 126, 155-164), was estimated at about 86,000.

The D-amino acid oxidase thus exists in its active form as a dimer with a molecular weight of about 86,000 and with two subunits.

Figure 3:
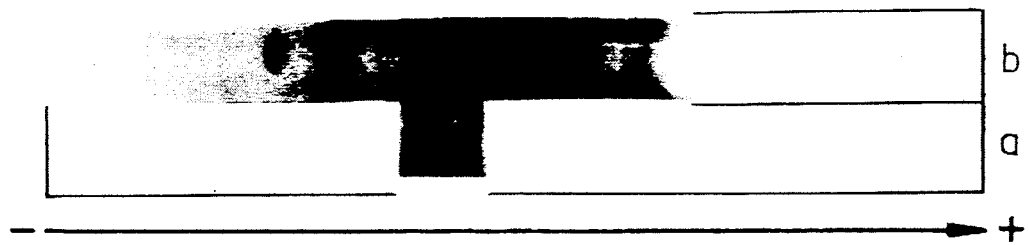
FIG. 3 shows activity staining of the gels in respect of D-amino acid oxidase. The illustrated fraction is taken from Step 3 according to the invention. The gels were incubated: a=with cephalosporin C, b=with D-leucine. The analysis was made as described below.

Enzymatic staining of the gels after incubation with D-leucine and cephalosporin C, respectively, showed only one band with the sample obtained after preparative gel electrophoresis, whereas the less purified preparation (Step 3) yielded three major bands after incubation with D-leucine and only one band with cephalosporin C (FIG. 3). This indicates the presence of several D-amino acid oxidases or isoenzymes in Trigonopsis, but only one of them exhibited activity against cephalosporin C. There is one report in the literature on the purification of D-amino acid oxidase from *Trigonopsis variabilis* (Berg, C. P., and Rodden, F. A. (1976) Anal. Biochem. 71, 214–222). However, the authors tested this protein only for activity against D-leucine. They did not check the homogeniety of the enzyme preparation. The procedure yields an impure mixture, some of the proteins of which are likely to represent amino acid oxidases.

The isolated D-amino acid oxidase having activity against cephalosporin C exhibited the following properties: The isoelectric point of the enzyme was about 4.6. Atomic absorption analysis strongly indicates that the enzyme contains two moles of iron which corresponds to one mole per subunit. After dialysis against 10 mM EDTA and 1 mM o-phenanthroline, respectively, the activity remained unchanged. Arsenite treatment reduced the activity to 46% and cyanide to 34% at a concentration of 0.5 mM. The $K_m$ values for cephalosporin C, phenylalanine, alanine, methionine and leucine were 13, 10, 76, 0.76 and 0.12, respectively. The sample obtained after preparative gel electrophoresis at a concetration of 5 mg/ml did not exhibit a spectrum similar to that of flavin-dependent enzymes, as may have been expected, since the amino acid oxidase obtained from hog kidney which is active against cephalosporin C is FAD-dependent (Mazzeo, P., and Romeo, A. (1972). J. C. S. Perkin I(P3), 2532). The addition of various flavin cofactors, such as FMN or FAD, did not increase the reduced specific activity Attempts to isolate flavins from the enzyme were unsuccessful. Thus, extensive dialysis against KBr in acid solution (Mayhew, S. G. (1971), Biochim. Biophys. Acta 235, 289–302), at alkaline pH (Massey, V., and Curti, B. (1966). J. Biol.Chem. 241, 3417–3429) all failed. Neither trypsinization, boiling or extraction with 85% phenol solution yielded any flavin. This is similar to the result reported in the literature on D-amino acid oxidase from *Aspergillus niger*, where the authors also were unable to detect any flavin (Kishore, G. and Vaidyanathan, C. S. (1976). Indian J. Biochem. Biophys. 13, 216–222).

The pure enzyme in 20 mM pyrophosphate buffer at pH8.3 was stable in the frozen state. Thawing and freezing did not destroy the activity. At 8° C., the activity dropped very slowly and the stability at room temperature was relatively low. To improve the thermal stability, the enzyme was immobilized by different methods. In one example, the addition of 17.5 U/ml of enzyme, obtained after Step 3, to 1 ml of CNBr-activated "Sepharose 4B" at 30° C. for 30 min. in 0.1 M borate buffer, pH 8.3, resulted in sustained activity of 7 U/ml "Sepharose".

By replacing the growth medium used by Berg and Rodden (Berg, C. P., and Rodden, F. A. (1976). Anal. Biochem. 71,214–222), the cultivation time could be reduced about 5 times in the present invention. The addition of 0.2% DL-methionine to the medium gave a fivefold increase of the enzyme yield.

We claim:

1. *Trigonopsis variabilis* D-amino acid oxidase which is active against the substrate cephalosporin C, said D-amino acid oxidase having an isoelectric point of about 4.6, existing in its active form as a dimer, having two subunits, and having a molecular weight of about 86,000.

2. An immobilized form of the D-amino acid oxidase of claim 1.

3. The immobilized D-amino acid oxidase of claim 2, wherein the D-amino acid oxidase is conjugated with cyanogen-bromide-activated Sepharose.

4. *Trigonopsis variabilis* D-amino acid oxidase active against cephalosporin C according to claim 1 produced by the process of
   (a) acidifying and heating a crude cell extract of *Trigonopsis variabilis* to obtain a precipitate and supernatant fraction;
   (b) treating said supernatant fraction obtained in step (a) with sufficient ammonium sulfate to obtain a second precipitate, said second precipitate containing said D-amino acid oxidase;
   (c) resuspending said precipitate obtained in step (b);
   (d) collecting said D-amino acid oxidase by isoelectric precipitation; and
   (e) purifying said D-amino acid oxidase by gel electrophoresis.

5. A method for isolating the D-amino acid oxidase of claim 1 from *Trigonopsis variabilis* which comprises:
   (a) acidifying a crude cell extract of *Trigonopsis variabilis* by adding acetic acid until the pH of said extract is about 5.3 to form a precipitate and supernatant fraction;
   (b) adding D,L-methionine to said supernatant to a final concentration of 25 mM;
   (c) heating said supernatant to 50° C. and maintaining it at 50° C. for ten minutes to form a second precipitate and supernatant fraction;
   (d) dialyzing said supernatant fraction obtained in step (c) against 20 mM sodium pyrophosphate buffer, pH 8.3;
   (e) adding solid ammonium sulfate to the solution prepared in step (d) to a final concentration of 30% and removing the resulting precipitate;
   (f) adding solid ammonium sulfate to the solution prepared in step (e) to a final concentration of 55% and collecting the resulting precipitate;
   (g) dialyzing said precipitate prepared in step (f) first against 20 mM sodium pyrophosphate buffer, pH 8.3, then against 25 mM sodium acetate buffer, pH 5.1, and removing any undissolved precipitate that remains after dialysis;
   (h) dialyzing the solution obtained in step (g) against 100 mM sodium acetate buffer, pH 4.6, and collecting the D-amino acid oxidase-containing precipitate; and
   (i) purifying said D-amino acid oxidase present in said D-amino acid oxidase-containing precipitate by preparative gel electrophoresis.

* * * * *